United States Patent
Kass et al.

(10) Patent No.: US 9,919,950 B2
(45) Date of Patent: Mar. 20, 2018

(54) LOW-BORON ZIRCONIUM-FREE NEUTRAL GLASS HAVING AN OPTIMIZED ALKALI METAL RATIO

(71) Applicant: SCHOTT AG, Mainz (DE)

(72) Inventors: Christof Kass, Tirschenreuth (DE); Stephan Tratzky, Neustadt/Wn. (DE); Reinhard Männl, Mitterteich (DE); Rainer Eichholz, Frankfurt am Main (DE)

(73) Assignee: SCHOTT AG, Mainz (DE)

(*) Notice: Subject to any disclaimer, the term of this patent is extended or adjusted under 35 U.S.C. 154(b) by 0 days.

(21) Appl. No.: 15/224,433

(22) Filed: Jul. 29, 2016

(65) Prior Publication Data

US 2017/0029319 A1    Feb. 2, 2017

(30) Foreign Application Priority Data

Jul. 29, 2015  (DE) .................. 10 2015 214 431

(51) Int. Cl.
| | |
|---|---|
| C03C 3/091 | (2006.01) |
| A61J 1/00 | (2006.01) |
| C03C 3/11 | (2006.01) |
| C03C 4/20 | (2006.01) |
| A61K 9/08 | (2006.01) |

(52) U.S. Cl.
CPC .............. C03C 3/091 (2013.01); A61J 1/00 (2013.01); A61K 9/08 (2013.01); C03C 3/11 (2013.01); C03C 4/20 (2013.01); *C03C 2204/00* (2013.01)

(58) Field of Classification Search
CPC ..................................... C03C 3/091
See application file for complete search history.

(56) References Cited

U.S. PATENT DOCUMENTS

| | | |
|---|---|---|
| 5,599,753 A | 2/1997 | Watzke et al. |
| 2003/0087745 A1 | 5/2003 | Peuchert et al. |
| 2004/0232576 A1 * | 11/2004 | Brodkin .................. C03C 3/091 264/16 |
| 2008/0057187 A1 * | 3/2008 | Trapp .................... C03C 17/003 427/169 |
| 2009/0315002 A1 * | 12/2009 | Ott .......................... C03C 3/118 252/588 |
| 2010/0317506 A1 | 12/2010 | Fechner et al. |
| 2011/0014475 A1 * | 1/2011 | Murata .................. C03B 17/064 428/410 |

FOREIGN PATENT DOCUMENTS

| | | | |
|---|---|---|---|
| DE | 4430710 | 5/1996 | |
| DE | 10027699 | 4/2002 | |
| DE | 10025465 | 8/2002 | |
| DE | 10120475 | 10/2002 | |
| DE | 10223889 A1 * | 1/2003 | ........... C03B 5/2252 |
| DE | 102010029975 | 12/2010 | |
| DE | 102014117640 A1 * | 6/2016 | ............. C03C 3/093 |
| FR | 2981930 A1 * | 5/2013 | ............. C03C 3/091 |

* cited by examiner

*Primary Examiner* — Elizabeth A. Bolden
(74) *Attorney, Agent, or Firm* — Ohlandt, Greeley, Ruggiero & Perle, L.L.P.

(57) ABSTRACT

A zirconium-free neutral glass is provided that finds use in the pharmaceutical sector. The glass has a combination of alkali metal oxides of sodium, potassium and optionally lithium, and a controlled amount of aluminum oxide, which provides a zirconium-free and low-boron neutral glass having good hydrolytic stability, good acid and alkali stability and good devitrification properties. The glass includes the following components in % by weight:

| | |
|---|---|
| $SiO_2$ | 72-82, |
| $B_2O_3$ | 3-8, |
| $Al_2O_3$ | 5-8, |
| $Na_2O$ | 2.5-5.5, |
| $K_2O$ | 3.6-8.4, |
| $Li_2O$ | 0-0.7, |
| $MgO$ | 0-0.7, |
| $CaO$ | 0-0.4, and |
| $TiO_2$ | 0-5, wherein |
| $Li_2O + Na_2O + K_2O$ | 6.8-14.6, and |
| $K_2O/Na_2O$ ratio | 0.7-3.4. |

20 Claims, No Drawings

LOW-BORON ZIRCONIUM-FREE NEUTRAL GLASS HAVING AN OPTIMIZED ALKALI METAL RATIO

CROSS REFERENCE TO RELATED APPLICATION

This application claims the benefit of benefit under 35 U.S.C. § 119(a) of German Application No. 10 2015 214 431.3 filed Jul. 29, 2015, the entire contents of which are incorporated herein by reference.

BACKGROUND

1. Field of the Invention

The invention relates to a zirconium-free neutral glass having a low boron oxide content and good hydrolytic stability for preferential use in the pharmaceutical sector.

2. Description of Related Art

In the pharmaceutical sector and for diagnostic and cosmetic applications, glass is employed as a packaging material on a large scale. Particularly the specific material properties thereof, such as high transparency, good mechanical properties and low permeability, in conjunction with good chemical stability, are crucial for the retention of the quality of medicaments, for example, and the efficacy thereof.

Containers for pharmaceutical, therapeutic, diagnostic and cosmetic purposes are generally in direct contact with the active ingredient contained therein and are therefore subject to strict demands. The containers, which may take the form, for example, of vials, ampoules, syringes or carpules, are therefore also referred to as primary packaging. During the storage of the active ingredients in the primary packaging, minimum loss of and no change in the active ingredients should occur. The quality of the contents must not be altered by direct contact with the primary packaging in such a way as to exceed the verified and stipulated limits. In each case, it has to be ensured that the glass material does not release any substances in amounts that impair the stability of the active ingredient or could even be toxic or harmful to a user in any other way.

Medicaments and other active ingredients are usually processed further and stored in dissolved form, especially on an aqueous basis. A particularly important property of a primary packaging made of glass is therefore the stability of the inner surface that comes into direct contact with the dissolved active ingredient and can be attacked thereby. This can cause various ions to be leached out of the glass surface and adversely affect the contents and active ingredient present therein. In order to rule out losses of action and especially health risks, therefore, generally as small an amount as possible of ions should be leached out of the glass. Since water-based solvents are the most commonly used, hydrolytic stability in particular is an important demand for the use of a glass as primary packaging. For acidic or basic solutions, corresponding demands on acid stability and alkali stability of the material of the packaging should be noted.

Hydrolytic class is also a basis for the classification of glass types for pharmaceutical uses according to the European Pharmacopoeia. Commonly used glasses are divided into classes. What are called type I glasses belong to hydrolytic class 1 and are also referred to as neutral glass. These also include the borosilicate glasses, which contain significant amounts of boron oxides, aluminium oxides or alkaline earth metal oxides.

It is known that an addition or increase in the proportion of boron oxide frequently leads to an improvement in hydrolytic stability, to lowering of the viscosity of the glass melt and to a reduction in the coefficient of expansion. Since these properties are particularly welcome for use as primary packaging in particular, the known glasses contain comparatively high boron oxide contents (up to 20%). Boron binds the alkali metal ions present more firmly into the glass structure. Because of the discovery that boron oxide is harmful to health, however, this concept is no longer justifiable. Boron oxide as an isolated substance is suspected of being teratogenic. This is of particular relevance for the production process of a glass, since complex health and safety measures are required when working with boron oxide as a starting component, and these increase the production costs of the end product. Boron components leached out of a glass could have an influence of toxicological concern on lifeforms.

Low-boron oxide (neutral) glasses are already known.

DE 4430710 C1 discloses a low-boric acid borosilicate glass having high chemical stability with the following composition in % by weight based on oxide:

| | |
|---|---|
| $SiO_2$ | >75, |
| $B_2O_3$ | 1-<9, |
| $Al_2O_3$ | 3-6, |
| $Li_2O$ | 0-4, |
| $Na_2O$ | 0-8, |
| $K_2O$ | 0-6, |
| $MgO$ | 0-3, |
| $CaO$ | 0-3, |
| $BaO$ | 0-2, |
| $SrO$ | 0-2, |
| $ZnO$ | 0-3, |
| $ZrO_2$ | 0-3, |
| $SnO_2$ | 0-3, |
| $SnO$ | 0-3, |
| $TiO_2$ | 0-2, |
| $CeO_2$ | 0-2, and |
| $Fe_2O_3$ | 0-1, wherein |
| $SiO_2 + B_2O_3$ | >83, |
| $SiO_2 : B_2O_3$ | >8, |
| $SiO_2 + Al_2O_3 + ZrO_2$ | >83, |
| $Li_2O + Na_2O + K_2O$ | 5-10, and |
| $MgO + CaO + BaO + SrO + ZnO$ | ≤3. |

According to the information in DE 4430710 C1, the glasses specified in the examples attain hydrolytic class HBK1 (according to the obsolete DIN 12111). However, determinations conducted in the context of the invention by the more modern method according to the United States Pharmacopeia (USP, see below) showed that the glass examples disclosed, in respect of the limit for hydrolytic class 1, are only in the moderate range and are therefore not competitive pharmaceutical glasses. Chemical stability is achieved in the glass examples described by means of high contents of zirconium oxide/$ZrO_2$ (up to 1.6% by weight) and/or relatively high boron oxide contents (up to 8.9% by weight).

The alkali metal content reported in the glass compositions specified by way of example is almost exclusively sodium oxide and lithium oxide. The sodium oxide content in the examples is above the inventive range. Potassium oxide is used only in example 5, but here in conjunction with a content of lithium oxide well above the inventive limit and a high zirconium oxide content. Measurements in the context of this invention have shown that such a composition gives rise to glasses having relatively poor values within the hydrolytic class HBK1 (high alkali metal ion release).

According to the disclosure of DE102010029975 A1, a low-boron oxide borosilicate glass having the following composition (in % by weight based on oxide) is described:

| | |
|---|---|
| $SiO_2$ | 70-79, |
| $B_2O_3$ | 0-<5, |
| $Al_2O_3$ | 1-<5, |
| $ZrO_2$ | 0.5-<5, |
| $TiO_2$ | 0.5-6, |
| $Na_2O$ | 1-6, |
| $K_2O$ | 3-8, and |
| $Li_2O$ | 0-0.5, wherein |
| $SiO_2 + B_2O_3$ | <83. |

To achieve the hydrolytic stability, the neutral glasses described therein necessarily contain zirconium oxide and titanium oxide in balanced mass ratios. The zirconium content here is also coupled to the potassium content, in order to establish the physical and chemical properties of the compositions. The good chemical properties of these glasses are attributed to the required content of zirconium oxide, titanium oxide and potassium oxide, and the interaction thereof in the glass.

It is known that zirconium oxide as a stabilizing additive promotes the chemical stability of glasses. It is used specifically for that purpose in DE 4430710 C1 and DE 102010029975 A1. To increase hydrolytic stability, it is used in DE 102010029975 A1 as a necessarily required constituent in combination with titanium oxide and in combination with potassium oxide in specific ratios for achievement of a synergistic effect. However, zirconium as a constituent of a neutral glass in the pharmaceutical sector is problematic, since these glasses require special approval and zirconium can be an unwanted constituent because it can include, inter alia, small amounts of uranium oxides and other radioactive substances (e.g. thorium compounds).

SUMMARY

It is an object of the present invention to propose a glass composition which substantially satisfies the demands for glasses that are to be used as primary packaging, especially in the pharmaceutical sector. These include, in particular, good hydrolytic stability, i.e. low ion release to an aqueous medium.

DETAILED DESCRIPTION

The zirconium (Zr)-free neutral glass which is preferably suitable for use in the pharmaceutical sector has the following composition in % by weight or consists thereof:

| | |
|---|---|
| $SiO_2$ | 72-82, |
| $B_2O_3$ | 3-8, |
| $Al_2O_3$ | 5-8, |
| $Na_2O$ | 2.5-5.5, |
| $K_2O$ | 3.6-8.4, |
| $Li_2O$ | 0-0.7, |
| MgO | 0-0.7, |
| CaO | 0-0.4, |
| $TiO_2$ | 0-5, wherein |
| $Li_2O + Na_2O + K_2O$ | 6.8-14.6% by weight, and |
| $K_2O/Na_2O$ ratio | 0.7-3.4. |

It will be apparent that the components in the glass composition are selected in such a way as to give a total of 100% by weight. Unless stated otherwise, all proportions stated are based on the finished glass compositions in the molten glass in % by weight based on the respective oxides.

The neutral glass according to the invention is classifiable in hydrolytic class 1 and also has good acid and alkali stability. According to the invention, it does not contain any added zirconium. Zirconium-free means here that no zirconium-containing compound is added to the starting mixture. Impurities may be present in the glass. The invention thus provides a glass which, by contrast with other primary packaging proposed for pharmaceutical packaging, does not require any special approval with regard to this constituent. Moreover, the glass of the invention contains a comparatively low level of boron oxide, especially by comparison with glasses that are currently in common use for the storage and packaging of injectables (e.g. FIOLAX® from SCHOTT). Containers used for primary packaging especially include vials, ampoules, carpules and syringes. These are typically produced by hot forming from a glass tube. Because of its technical and physical properties, the glass of the invention is suitable for glass tube production. By virtue of the low boron oxide content, there is a much lower level of borate evaporation in the course of hot shaping and forming than in the case of the glasses used conventionally. Especially in the case of further processing to give vials, significant boron vaporization in parts of the inner surfaces can cause corrosion effects which, in the later use of such damaged vials, lead to an increased risk of delamination, this being understood to mean the detachment of macroscopic glass flakes from the wall, and to an increased release of alkali metal from glass containers according to ISO 4802-1 and -2. These adverse effects are reduced in the case of a neutral glass of the invention.

In the context of the invention, it has been found that, unexpectedly, the controlled choice of amounts of the alkali metal oxides of sodium, potassium and optionally lithium in the glass composition and the establishment of a particular ratio of potassium oxide to sodium oxide results in an unforeseeable hydrolytic stability of the neutral glass produced, without the addition of the zirconium oxide required in the prior art glasses. It is also surprising that this effect (firm binding of the alkali metal ions into the glass structure) is established even though the glass of the invention has a comparatively low boron oxide content compared to customary borosilicate glasses.

As well as the $K_2O/Na_2O$ ratio specified and described in detail below, which has to be set within the range specified, the other components of the glass composition also play a role.

$SiO_2$ as a main constituent of the glass composition is a significant glass former and has the effect that the glass is sufficiently stable and durable. According to the invention, the proportion is in the range from 72% to 82% by weight. Advantageously, it may also be in the range from 75% to 81% by weight, preferably in the range from 77% to 80% by weight. In the composition of the invention, at least 72% by weight of $SiO_2$ is present. A smaller amount would impair the hydrolytic stability of the glass. According to the invention, the upper limit is 82% by weight. Higher proportions of $SiO_2$ would excessively increase the melting temperature and processing temperature of the glass (i.e. the temperature at which the glass has a viscosity suitable for processing, which is approximately $10^4$ dPas). The lower $SiO_2$ limit in an advantageous glass composition may also be 75% by weight, preferably 77% by weight. The upper $SiO_2$ limit chosen in advantageous embodiments may be 81% by weight, preferably 80% by weight.

$B_2O_3$, like $SiO_2$, is a glass former and is used in glasses to achieve good hydrolytic stability, to lower viscosity and to reduce the coefficient of expansion. According to the invention, boron oxide is present in the glass composition in the range from 3% to 8% by weight, preferably in the range from 3% to 6.5% by weight, more preferably in the range from 3.5% to 5.5% by weight. Since boron oxide binds the alkali metal ions into the glass structure, according to the invention, at least 3% by weight of $B_2O_3$ is present in the glass composition. The inventive proportion of $B_2O_3$ in the glass is limited to not more than 8% by weight, in order to minimize the abovementioned evaporation of borates, especially in the formation of the container bases, and the associated problems. In some glasses, 3.5% by weight may also be chosen as an advantageous lower limit for boron oxide. Advantageous embodiments of the invention contain a maximum of only 6.5% by weight of $B_2O_3$, and particularly preferred embodiments only 5.5% by weight of $B_2O_3$. Compared to conventional type I pharmaceutical glasses that are available (e.g. Fiolax® from SCHOTT), the glass according to the invention has a reduced, preferably greatly reduced, boron oxide content and nevertheless, by comparison, has improved hydrolytic stability.

The content of $Al_2O_3$ in the glass composition according to the invention is 5% to 8% by weight, preferably 5% to 7.5% by weight. Aluminium is used as a network former and contracts the complete glass structure. The gaps in the glass network for the cations become smaller as a result. The tighter structure results in a lower release of alkali metal on leaching by aqueous solutions. Moreover, the addition of aluminium oxide improves the devitrification properties (see below). According to the invention, the $Al_2O_3$ content should not go below a minimum level of 5% by weight, in order that there is no troublesome crystal formation (also called devitrification) in the course of shaping (for example during the process of drawing a glass tube). Since aluminium increases the melting temperature and processing temperature of the glass composition, according to the invention, a maximum of 8% by weight of aluminium oxide is envisaged. Advantageous embodiments may also contain a maximum of 7.5% by weight of $Al_2O_3$. The proportion of aluminium oxide in the glass composition also depends on the chosen method by which the molten glass is brought into shape (for example drawn as a tube).

Oxides of potassium, sodium and optionally lithium play a role in adjusting thermal expansion (coefficient of thermal expansion), improve the meltability of the glass and reduce the viscosity. According to the invention, the sum total of the alkali metal oxides is in the range from 6.8% to 14.6% by weight. In advantageous embodiments, the sum total of the alkali metal oxides may also be 6.8% to 13.3% by weight, preferably 7% to 12.6% by weight. The sum total of alkali metal oxide should not go below a minimum level of 6.8% by weight, since the meltability of the glasses obtained otherwise deteriorates excessively. Above the sum total of alkali metal oxide of 14.6% by weight, the chemical stability of the glasses deteriorates. In the case of an advantageous glass composition, the lower limit for the sum total of the alkali metal oxides may also be 7% by weight. With regard to the upper limit, alkali metal oxides can advantageously also be used with a sum total of 13.3% by weight, preferably with a sum total of 12.6% by weight.

According to the invention, it is possible to add lithium oxide with a proportion of 0% to 0.7% by weight to the glass composition. Preference is given to an $Li_2O$ content of 0% to 0.5% by weight. $Li_2O$ can be used in some glass compositions in order to lower the processing temperature. Since lithium has a very small ionic radius, there is the risk of leaching out of the gaps in the glass structure. Therefore, the maximum $Li_2O$ content of 0.7% by weight should not be exceeded, in order not to lower the hydrolytic stability. It may also be advantageous when the glass composition contains a maximum of 0.5% by weight of $Li_2O$. Preferably no lithium is added.

$Na_2O$ is used in glasses because sodium in conjunction with aluminium improves the hydrolytic stability thereof. Moreover, sodium lowers the melting temperature. According to the invention, the sodium oxide content is in the range from 2.5% to 5.5% by weight, preferably in the range from 2.8% to 4.8% by weight. A glass of the invention thus contains at least 2.5% by weight of sodium oxide. The upper limit for $Na_2O$ of not more than 5.5% by weight should not be exceeded, since the chemical stability otherwise worsens. It may be advantageous to provide at least 2.8% by weight of $Na_2O$ in the glass. Preferably, the upper limit for sodium oxide may also be 4.8% by weight.

The $K_2O$ content of the glass composition of the invention is 3.6% to 8.4% by weight. In an advantageous embodiment, it is in the range from 4% to 8% by weight, preferably in the range from 4.2% to 7.8% by weight. Potassium results in good hydrolytic stability and improves the devitrification properties of the glass. In order to achieve this effect, the inventive lower limit for potassium oxide is 3.6% by weight. According to the invention, not more than 8.4% by weight of $K_2O$ is used, since the chemical stability of the glass deteriorates above this level. The lower $K_2O$ limit in the case of an advantageous glass composition may also be 4% by weight, preferably 4.2% by weight. An upper limit chosen in advantageous embodiments may be 8% by weight of $K_2O$, preferably 7.8% by weight of $K_2O$.

In the context of the invention, it has been found that it is not just the above-described individual amounts of sodium oxide, potassium oxide and optionally lithium oxide and the above-described sum total thereof in the glass that play an important role in terms of chemical stability. In addition, in accordance with the invention, a specific ratio of potassium oxide and sodium oxide is established in the glass composition. According to the invention, a $K_2O/Na_2O$ ratio of 0.7 to 3.4 is present in the glass. Surprisingly, the alkali metal ions, on establishment of such a ratio, are firmly incorporated into the glass structure, even though the glass composition contains no zirconium oxide ($ZrO_2$) and only a relatively small amount of boron oxide. The neutral glasses of such a composition have very good chemical stability, especially excellent hydrolytic stability. They do not just attain hydrolytic class 1, but are within the upper quarter to upper third within this class, in respect of the upper limit (see Table 1). This is of particular significance for uses in the pharmaceutical sector, since leaching of ions out of the glass can harbour health risks. In this regard, the glasses of the invention are much better than the low-boron oxide, zirconium-containing neutral glasses known from the prior art. With regard to acid stability (determined according to DIN 12116) and alkali stability (determined according to ISO 695) as well, the glasses according to the invention have better values than known neutral glasses. A $K_2O/Na_2O$ ratio of <0.7 should not be established because there would otherwise be a deterioration in the release of sodium and the devitrification properties. The upper limit in the $K_2O/Na_2O$ ratio of 3.4 should also be observed, because evaporation losses of potassium on melting become too high above this level.

In advantageous embodiments, a $K_2O/Na_2O$ ratio of preferably 0.8 to 2.9, more preferably of 0.9 to 2.8, is present. A lower limit in the K$_2$O/Na$_2$O ratio may advantageously be 0.8, preferably 0.9. An upper limit in the K$_2$O/Na$_2$O ratio may advantageously be 2.9, preferably 2.8.

A particularly preferred glass composition includes 3.5% by weight of Na$_2$O and 6.5% by weight of K$_2$O and hence a K$_2$O/Na$_2$O ratio of 1.86.

Alkaline earth metal oxides may be present in the glass composition in small amounts. The CaO content in the glass according to the invention is in the range from 0% to 0.4% by weight. The MgO content in the glass according to the invention is in the range from 0% to 0.7% by weight. Above the limits mentioned, there is a deterioration in the hydrolytic stability of the neutral glasses. Preference is given to adding no CaO and/or no MgO to the glass composition. Barium ions can leach out of the glass structure only to a minor degree, but are undesirable in the pharmaceutical industry since precipitates occur in the case of particular fillings. Preferably, the neutral glass does not contain any BaO. An advantageous glass composition does not contain any alkaline earth metal oxide, meaning that alkaline earth metal oxide is not added to the starting mixture. However, impurities may be present in the glass.

The TiO$_2$ content in the glass of the invention is in the range from 0% to 5% by weight. Titanium oxide can lower the viscosity of the neutral glass. In addition, it provides protection from UV radiation and prevents solarization (darkening caused by the effect of light). The upper limit of 5% by weight of TiO$_2$ should not be exceeded, since the devitrification properties of the resulting glass would otherwise deteriorate. Advantageous embodiments do not contain any added TiO$_2$.

In the production process for the glass according to the invention, also added to the blend of the starting components in a known manner are refining agents (for example antimony oxide, cerium oxide, tin oxide, chlorides) and fusion accelerators (for example fluorides) in known amounts, and these—according to the material used—may still be present in the finished glass (e.g. fluorides 0% to 1% by weight, chlorides 0% to 0.5% by weight).

The inventive specific combination of the alkali metal oxides of sodium, potassium and optionally lithium, and a controlled amount of aluminium oxide, provide an inventive zirconium-free, low-boron neutral glass which, as well as excellent hydrolytic stability and very good acid and alkali stability, features stability to crystallization and only a very low tendency to devitrification, if any.

A glass composition according to the invention leads to a neutral glass which is producible in tubular form (for example can be drawn to a tube) and is advantageously suitable for further processing to give containers such as ampoules, carpules, syringes, etc. Alternatively, it is also possible to produce other forms from the glass, for example flat glasses, glass blocks, etc. Compared to known glasses (e.g. DE102010029975 A1), the neutral glass of the invention features lower borate evaporation and higher crystallization stability, such that it can also be drawn to a tube by the Danner process. Other tube drawing methods are of course also possible, for example the Vello drawing process.

An advantageous embodiment relates to a zirconium-free neutral glass having high hydrolytic stability, having a composition comprising, in % by weight:

| | |
|---|---|
| SiO$_2$ | 75-81, |
| B$_2$O$_3$ | 3-6.5, |
| Al$_2$O$_3$ | 5-7.5, |
| Na$_2$O | 2.8-4.8, |
| K$_2$O | 4.0-8.0, and |
| Li$_2$O | 0-0.5, where |
| Li$_2$O + Na$_2$O + K$_2$O | 6.8-13.3, and |
| K$_2$O/Na$_2$O ratio | 0.8-2.9. |

These are supplemented by customary refining agents in customary amounts.

A particularly advantageous embodiment relates to a zirconium-free neutral glass having high hydrolytic stability, having a composition comprising, in % by weight:

| | |
|---|---|
| SiO$_2$ | 77-80, |
| B$_2$O$_3$ | 3.5-5.5, |
| Al$_2$O$_3$ | 5.0-7.5, |
| Na$_2$O | 2.8-4.8, and |
| K$_2$O | 4.2-7.8, wherein |
| Li$_2$O + Na$_2$O + K$_2$O | 7.0-12.6, and |
| K$_2$O/Na$_2$O ratio | 0.9-2.8. |

These are supplemented by customary refining agents in customary amounts.

The invention also relates to a drawn tube consisting of or comprising the glass according to the invention. Moreover, the invention also relates to the use of the glass according to the invention for production of a drawn tube.

The invention also provides for the use of a neutral glass according to the invention in the pharmaceutical sector. More particularly, the glass can be used for vials, syringes, ampoules and/or carpules. The invention likewise provides such a container produced from the glass according to the invention.

In addition, the glass according to the invention, because of its chemical stability, may find use as laboratory glass (for example for a piece of laboratory equipment such as a pipette, burette, beaker, test tube, flask, measuring flask, cylinder, measuring cylinder, condenser, cold trap, funnel, dish, U-tube, Dewar vessel, thermometer, etc.), both in the pharmaceutical sector and in the nonpharmaceutical sector. The invention likewise provides a piece of laboratory equipment produced from the glass according to the invention.

The invention further provides for the use of a neutral glass according to the invention as a primary packaging, preferably as a primary packaging for medicaments, especially for aqueous or water-containing medicaments.

The term "primary packaging" should be understood in a broad sense in the context of the invention and encompasses any type, size and shape of glass container in the broadest sense. This includes any kind of hollow body made from glass which is closeable and can be used in the pharmaceutical sector (for example bottles, vials, phials, ampoules, carpules, syringes, etc.).

In the context of the invention, "aqueous or water-containing medicament" is understood to be any kind of medicament active ingredient, including mixtures of two or more medicament active ingredients that contain(s) water.

"Aqueous medicament" is understood to mean a medicament having water as the main constituent. For example, water may constitute the main constituent of the dispersion medium in which the medicament active ingredient(s) is/are dispersed. For example, an aqueous solution with the medicament active ingredient dissolved therein may be present, for example an injection solution.

"Water-containing medicament" is also understood to mean a medicament that does not have water as the main constituent. For example, this may be a water-containing medicament, for example a solution, having a proportion of water and other solvents, for example alcohol, in which at least one medicament active ingredient is dispersed or dissolved.

The medicament may also be in liquid form. However, this need not always be the case. There are also semisolid or solid medicament formulations (for example a powder) which may be present in primary packaging according to the invention.

The glasses of the present invention have advantageous properties that are required for the faultless and inexpensive mass production thereof, especially for production of primary pharmaceutical packaging. They fulfill the necessary prerequisites with regard to melting characteristics, crystallization stability, refining properties, processibility and chemical stability (especially hydrolytic stability). Thus, the neutral glasses according to the invention are particularly suitable for production of primary pharmaceutical packaging. They have good meltability and can be drawn efficiently to give tubes. Pharmaceutical containers such as primary packaging made from glass are typically manufactured by hot forming from glass tubes, and so the production of glass tubes is of particular significance. Overall, the glasses according to the invention are producible in an economically viable manner in sufficiently good quality on the industrial scale.

The invention also relates to a primary packaging which consists of a neutral glass according to the invention. Medicaments stored in the primary packaging according to the invention, especially aqueous or water-containing medicaments, for example injection solutions, do not significantly attack the inner surface of the container, such that only few ions, if any, are released from the glass.

Since the neutral glass according to the invention is chemically stable (chemically inert) in contact with water, active ingredients and/or buffer systems in the pH range from 1 to 11, it is of excellent suitability for production of pharmaceutical containers (primary packaging). A container produced from the glass according to the invention can thus be used particularly well for the storage of water, an active ingredient and/or a buffer solution in the pH range from 1 to 11.

A pharmaceutical container manufactured from the neutral glass according to the invention is advantageously suitable for storage of water and/or an active ingredient and/or a buffer solution in the pH range from 4 to 9 (e.g. 1 molar or 8.4% sodium bicarbonate solution $NaHCO_3$ having a pH of about 8).

Preference is given to a pharmaceutical container, manufactured from the neutral glass according to the invention, which is suitable for storage of an active ingredient and/or a buffer solution in the pH range from 5 to 7 (for example for a 10 mmolar citrate buffer (pH=6) with 150 mmolar NaCl and 0.005% Tween 20 or for a 10 mmolar phosphate buffer (pH=7) with 150 mmolar NaCl and 0.005% Tween 20) and/or for storage of water, especially of water for injection purposes (e.g. Sartorius ultrapure water, flushed through 0.2 µm filter, with resistivity 18.2 MΩ×cm).

The invention thus also provides a primary packaging produced from the neutral glass according to the invention, containing at least one component selected from the group of water, active ingredient, buffer solution in the pH range of 1 to 11.

The invention further provides a primary packaging produced from the neutral glass according to the invention, containing at least one component selected from the group of water, active ingredient, buffer solution in the pH range of 4 to 9.

The invention additionally provides a primary packaging produced from the neutral glass according to the invention, containing at least one component selected from the group of water, active ingredient, buffer solution in the pH range of 5 to 7.

The invention further provides a primary packaging produced from the neutral glass according to the invention, containing water for injection purposes.

The present invention is elucidated hereinafter by examples, which illustrate the teaching according to the invention but are not intended to restrict it.

EXAMPLES

It should be noted that the amounts of the components stated in the tables which follow are amounts that are present in the molten glass. The person skilled in the art will be aware that some components (e.g. boron oxide (boric acid, alkali metal borates)) have a tendency to evaporate in the process for producing the glass and in forming processes. In the case of these components, the amount present in the starting composition is thus greater than in the molten glass at a later stage. Moreover, the person skilled in the art will be familiar with the fact that the melting temperatures required and temperatures during the processing affect the extent of evaporation, such that he is able to specifically calculate the amounts to be used. The evaporation of the volatile components leads to greater amounts of nonvolatile components remaining in the molten glass.

Seven working examples have been selected by way of example from the glass composition range according to the invention (see Table 1). The production process comprised the steps of: mixing the glass components, melting the glass components and refining the glass melt. Subsequently, tubes or tube sections were produced (drawn by the Danner process).

The physical and chemical properties of the samples produced from the glass examples were determined.

The property of hydrolytic stability which is particularly important in the case of neutral glasses for the pharmaceutical sector and the classification were determined by the standardized "Glass Grains Test" according to the United States Pharmacopeia (USP 38, Ch. 660 "Containers-Glass").

The classification of glasses according to USP 38 in 3 types (type I, type II, type III) is effected by the following method:

Cleaning the starting glass to be tested, comminuting in a mortar or in a ball mill, sieving with three different standardized sieve mesh sizes, repeated cleaning with acetone in an ultrasound bath and drying—all in accordance with a sequence set out specifically in the USP. Glass grains having a defined particle size are obtained.

In a flask, 10 g of glass grains are admixed with 50 ml of carbon dioxide-free purified water (glass sample). The closed flask is autoclaved under specified conditions for 30 min (+/−1 min) at 121° C. (+/−1° C.) and cooled down, as is a corresponding blank sample without glass grains. Subsequently added to the blank sample and the glass sample is 0.05 ml of methyl red solution (which has been prepared according to USP specifications), and titration is effected with 0.02 M hydrochloric acid until the colour changes from red to yellow. After subtracting the titration volume of the blank sample from the titration volume of the glass sample, the result is calculated in ml of 0.02 M hydrochloric acid consumed per g of sample.

If the volume of the 0.02 M hydrochloric acid consumed per gram of sample is not more than 0.1 ml, the glasses are type I glasses, i.e. glasses that belong to hydrolytic class 1. Glasses where not more than 0.85 ml of 0.02 M hydrochloric acid was consumed per gram of sample are type II or type III glasses.

The volume of hydrochloric acid required in the titration is a measure of the (alkali metal) leaching out of the glass of the invention. The tables which follow show, under USP, the hydrolytic stability of the working examples (Table 1) and the comparative examples (Table 2). All the glasses mentioned belong to hydrolytic class 1, which was determined predominantly by the USP method. Comparative examples C7 to C10, corresponding to Ex. 1 to Ex. 4 of DE102010029975A1, contain data which were determined according to the known ISO 719 in μg/g. In order to make the hydrolytic data determined by different methods comparable, it is possible to infer, from the figure "% of the limit", the region within hydrolytic class 1 where a glass is present. This feature is thus a quality feature of the glass. The lower it is, the better the hydrolytic stability of the particular glass. Thus, it can clearly be inferred from the tables that the working examples manufactured according to the invention have better hydrolytic stability than known neutral glasses, some of which are already being used in the pharmaceutical sector. This means that fewer ions are released from the zirconium-free, low-boron neutral glass according to the invention than from other pharmaceutical glasses.

Of the hydrolytic classes, a distinction should be made between the acid classes according to DIN 12116 and the alkali classes according to ISO 695. Overall, the measurements from the working examples show that the neutral glass according to the invention is also better in terms of alkali and acid stability than current pharmaceutical glasses.

In the working examples, no devitrification occurs apart from one example. Devitrification, i.e. crystal growth in the glass (crystallization rate CR (in μm/min)) was determined by the known standard ASTM C829-81. Because of the high crystallization stability, the glasses according to the invention are suitable for drawing by the Danner process. The coefficient of thermal expansion (CTE, in $10^{-6} K^{-1}$) also meets the demands on a neutral glass, especially for the pharmaceutical sector. As does the transformation temperature Tg (° C.).

The results thus show that the neutral glasses according to the invention are suitable for the preferred use as primary packaging in the pharmaceutical sector and can especially be used for aqueous or water-containing medicaments. The medicaments stored in the containers according to the invention do not attack the glass to a significant degree.

TABLE 1

Compositions (all figures in % by weight) and physical properties of the inventive working examples

| | A1 | A2 | A3 | A4 | A5 | A6 | A7 |
|---|---|---|---|---|---|---|---|
| Constituent: | | | | | | | |
| $SiO_2$ | 77.7 | 79 | 79.7 | 78.95 | 78.1 | 80.35 | 79.9 |
| $B_2O_3$ | 4.5 | 4.6 | 3.6 | 3.1 | 7.7 | 3 | 4.7 |
| $Al_2O_3$ | 7.3 | 6.55 | 6.4 | 6.4 | 5.2 | 6.5 | 7 |
| $Na_2O$ | 3.1 | 3.1 | 3.3 | 3.25 | 2.9 | 3.2 | 4.5 |
| $K_2O$ | 6.3 | 6.3 | 6.5 | 6.5 | 6.1 | 6.9 | 3.8 |
| MgO | — | — | — | — | — | — | — |
| CaO | — | — | — | — | — | — | — |
| BaO | — | — | — | — | — | — | — |
| $TiO_2$ | 0.7 | — | — | 1.4 | — | — | — |
| $ZrO_2$ | — | — | — | — | — | — | — |
| $Li_2O$ | 0.3 | 0.35 | 0.4 | 0.3 | — | 0 | — |
| Cl | 0.05 | 0.05 | 0.05 | 0.05 | 0.05 | 0.05 | 0.05 |
| $Fe_2O_3$ | | | | | | | |
| $MnO_2$ | | | | | | | |
| Sum total | 100 | 100 | 100 | 100 | 100 | 100 | 100.0 |
| $N_2O + K_2O + Li_2O$ | 9.7 | 9.75 | 10.2 | 10.05 | 9 | 10.1 | 8.3 |
| $K_2O/Na_2O$ | 2.03 | 2.03 | 1.97 | 2.00 | 2.10 | 2.16 | 0.84 |
| $SiO_2 + B_2O_3$ | 82.20 | 83.60 | 83.30 | 82.05 | 85.80 | 83.35 | 84.60 |
| Physicochemical properties: | | | | | | | |
| Devitrification | none | none | none | none | 0.1 | none | none |
| USP [mg/l] Class | 0.0251 | 0.0231 | 0.0261 | 0.0291 | 0.0211 | 0.0291 | 0.0181 |
| % of the limit | 25% | 23% | 26% | 29% | 21% | 29% | 18% |
| DIN 12116 [mg/l] | 0.3 | 0.3 | 0.3 | 0.3 | 0.3 | 0.3 | 0.3 |
| ISO 695 [mg/l] | 81 | 86 | 93 | 91 | 87 | | 79 |
| CTE | 5.37 | 5.5 | 5.64 | — | 5.30 | 5.60 | 4.95 |
| Tg | 568 | 563 | 562 | 585 | | | 565 |

TABLE 2

Compositions (all figures in % by weight) and physical properties of the comparative examples

| | Comparative examples | | | | | | | |
|---|---|---|---|---|---|---|---|---|
| | C11 | C12 | C13 | C14 | C1 | C2 | C3 | |
| Constituent: | | | | | | | | |
| $SiO_2$ | 79.4 | 75.5 | 73 | 72.2 | 74 | 71 | 66.92 | |
| $B_2O_3$ | 2.7 | 10.3 | 11.1 | 10.2 | 4.9 | 5.6 | 6 | |
| $Al_2O_3$ | 5 | 5.45 | 7.1 | 7.2 | 4.75 | 6.5 | 4.5 | |
| $Na_2O$ | 3.2 | 7.3 | 7.55 | 6.2 | 8.75 | 8.93 | 6.9 | |
| $K_2O$ | 8.4 | — | 0.65 | 1.95 | 2.1 | 2.57 | 2.8 | |
| MgO | — | — | — | — | | | | |
| CaO | 1 | 1.45 | 0.55 | 0.75 | 3.3 | 3.3 | 4.2 | |
| BaO | — | — | — | 1.35 | 2.2 | 2.1 | 1.6 | |
| $TiO_2$ | 2 | — | — | — | — | — | 0.4 | |
| $ZrO_2$ | — | — | — | — | | | | |
| $Li_2O$ | 0.3 | — | — | — | — | — | 0.1 | |
| Cl | 0.05 | — | 0.15 | 0.09 | | | | |
| $Fe_2O_3$ | | | | | | | 1.8 | |
| $MnO_2$ | | | | | | | 4.78 | |
| Sum total | 100 | 100 | 100 | 100 | | | | |
| $N_2O + K_2O + Li_2O$ | 9.9 | 7.3 | 8.1 | 8.15 | 10.85 | 11.5 | | |
| $K_2O/Na_2O$ | 2.00 | — | 0.07 | 0.31 | 0.24 | 0.29 | 0.41 | |
| $SiO_2 + B_2O_3$ | 82.10 | 85.80 | 84.10 | 82.40 | 78.90 | 76.60 | 72.92 | |
| Physicochemical properties: | | | | | | | | |
| Devitrification | 0.2 | 0.2 | none | 0.05 | | | | |
| USP [mg/l] | 0.061 | 0.051 | 0.0381 | 0.0351 | 0.0691 | 0.071 | 0.0661 | ISO 719 [µg/g] |
| Class | | | | | | | | |
| % of the limit | 60% | 50% | 38% | 35% | 69% | 70% | 66% | |
| DIN 12116 [mg/l] | | 0.4 | 0.4 | 0.6 | — | — | — | |
| ISO 695 [mg/l] | | 115 | 125 | 140 | — | — | — | |
| CTE | 5.80 | 4.90 | 5.20 | 5.31 | 6.7 | 7.2 | 6.76 | |
| Tg | — | 565 | 550 | 560 | 587 | 553 | 550 | |

Compositions (all figures in % by weight) and physical properties of the comparative examples

| | Comparative examples | | | | | | | |
|---|---|---|---|---|---|---|---|---|
| | C4 | C5 | C6 | C7 | C8 | C9 | C10 | |
| $SiO_2$ | 71 | 80 | 80.5 | 76.3 | 75.9 | 75.9 | 73.3 | |
| $B_2O_3$ | 6.2 | 5.3 | 5.3 | 3.05 | 4.7 | 4.7 | 4.8 | |
| $Al_2O_3$ | 5.75 | 4.7 | 4.8 | 3.7 | 3 | 3 | 3 | |
| $Na_2O$ | 11.4 | 2.6 | 6.8 | 3.78 | 4 | 4 | 4 | |
| $K_2O$ | 0.35 | 4 | — | 6.6 | 6.6 | 7 | 6.6 | |
| MgO | | | | — | — | — | — | |
| CaO | 3.2 | 0.3 | 0.3 | — | — | — | — | |
| BaO | 2 | 0.2 | 0.2 | — | — | — | — | |
| $TiO_2$ | 0.1 | — | — | 2.7 | 2.7 | 3 | 5 | |
| $ZrO_2$ | | 1.6 | 1.6 | 3.8 | 3 | 3 | 3 | |
| $Li_2O$ | — | 1.3 | 0.5 | 0.3 | 0.3 | 0.3 | 0.3 | |
| Cl | | | | | | | | |
| $Fe_2O_3$ | | | | | | | | |
| $MnO_2$ | | | | | | | | |
| Sum total | | | | 100 | 100 | 100 | 100 | |
| $N_2O + K_2O + Li_2O$ | | | | 10.69 | 10.9 | 11.3 | 10.9 | |
| $K_2O/Na_2O$ | 0.03 | 1.54 | — | 1.75 | 1.65 | 1.75 | 1.65 | |
| $SiO_2 + B_2O_3$ | 77.20 | 85.30 | 85.80 | 79.35 | 80.60 | 80.60 | 78.10 | |
| Physicochemical properties: | | | | | | | | |
| Devitrification | 0.11 | 0.0381 | 0.0421 | 111 | 121 | 141 | 131 | ISO 719 [µg/g] |
| USP [mg/l] | | | | | | | | |
| Class | | | | | | | | |
| % of the limit | 100% | 38% | 42% | 35% | 39% | 45% | 42% | |
| DIN 12116 [mg/l] | — | — | — | — | — | — | — | |
| ISO 695 [mg/l] | — | — | — | — | — | — | — | |
| CTE | 7.3 | 4.4 | 5.3 | — | — | — | — | |
| Tg | 549 | 562 | 516 | — | — | — | — | |

What is claimed is:

1. A neutral glass that is free of zirconium and comprises the following components in % by weight:

| | |
|---|---|
| $SiO_2$ | 72-82, |
| $B_2O_3$ | 3-8, |
| $Al_2O_3$ | 5-8, |
| $Na_2O$ | 2.5-5.5, |
| $K_2O$ | 3.6-8.4, |
| $Li_2O$ | 0-0.7, |
| MgO | 0-0.7, |
| CaO | 0-0.4, and |
| $TiO_2$ | 0-5, wherein |
| $Li_2O + Na_2O + K_2O$ | 6.8-14.6, and |
| $K_2O/Na_2O$ ratio | 0.7-3.4. | wherein the neutral glass is free of zirconium.

2. The neutral glass according to claim 1, wherein the $SiO_2$ has a content in a range from 75% to 81% by weight.

3. The neutral glass according to claim 1, wherein the $SiO_2$ has a content in a range from 77% to 80% by weight.

4. The neutral glass according to claim 1, wherein the $B_2O_3$ has a content in a range of 3%-5.5% by weight.

5. The neutral glass according to claim 1, wherein the $B_2O_3$ has a content in a range of 3.5%-5.5% by weight.

6. The neutral glass according to claim 1, wherein the $Al_2O_3$ has a content in a range from 5% to 7.5% by weight.

7. The neutral glass according to claim 1, wherein the components do not contain any BaO.

8. The neutral glass according to claim 1, wherein the $Na_2O$ has a content in a range of 2.8%-4.8% by weight.

9. The neutral glass according to claim 1, wherein the $K_2O$ has a content in a range of 4%-8% by weight.

10. The neutral glass according to claim 1, wherein the $K_2O$ has a content in a range of 4.2%-7.8% by weight.

11. The neutral glass according to claim 1, comprising 3.5% by weight of $Na_2O$ and 6.5% by weight of $K_2O$.

12. The neutral glass according to claim 1, wherein the $LiO_2$ has a content in a range of 0%-0.5% by weight.

13. The neutral glass according to claim 1, further comprising a sum total of $Na_2O+K_2O+Li_2O$ in a range between 6.8% and 13.3% by weight.

14. The neutral glass according to claim 1, further comprising a sum total of $Na_2O+K_2O+Li_2O$ in a range between 7.0% and 12.6% by weight.

15. The neutral glass according to claim 1, wherein the $K_2O/Na_2O$ ratio is in a range from 0.8 to 2.9.

16. The neutral glass according to claim 1, wherein the $K_2O/Na_2O$ ratio is in a range from 0.9 to 2.8.

17. The neutral glass according to claim 1, wherein the components do not contain any alkaline earth metal oxide.

18. The neutral glass according to claim 1, wherein the glass is suitable for a use selected from the group consisting of a drawn tube, a vial, a syringe, an ampoule, a carpule, a primary pharmaceutical packaging, and primary pharmaceutical packaging for aqueous or water-containing medicaments.

19. A primary pharmaceutical packaging comprising a neutral glass according to claim 1.

20. The primary packaging according to claim 19 further comprising at least one component selected from the group consisting of water, active ingredient, and buffer solution in the pH range of 1 to 11.

* * * * *